United States Patent [19]
Resch

[11] Patent Number: 5,159,247
[45] Date of Patent: Oct. 27, 1992

[54] RAIN-ACTUATED CONTROL FOR COVERING SYSTEMS

[75] Inventor: Martha Resch, Pocking, Fed. Rep. of Germany

[73] Assignees: Armin Sattlecker, Burghausen; Hans Högen, Trostberg, both of Fed. Rep. of Germany

[21] Appl. No.: 571,669

[22] PCT Filed: Jan. 3, 1990

[86] PCT No.: PCT/DE90/00001
§ 371 Date: Aug. 30, 1990
§ 102(e) Date: Aug. 30, 1990

[87] PCT Pub. No.: WO90/07437
PCT Pub. Date: Jul. 12, 1990

[30] Foreign Application Priority Data

Jan. 5, 1989 [DE] Fed. Rep. of Germany ....... 3900184
Jun. 5, 1989 [DE] Fed. Rep. of Germany ....... 3918331

[51] Int. Cl.$^5$ .................. B60J 7/057; B60R 16/02; E05F 15/20
[52] U.S. Cl. .................................. 318/483; 318/466; 49/31
[58] Field of Search ......... 318/443, 444, 483, DIG. 2, 318/453, 466, 467, 468; 15/250 C, 250.05, 250.17; 49/21, 23, 24, 31

[56] References Cited

U.S. PATENT DOCUMENTS

| | | | |
|---|---|---|---|
| 3,826,979 | 7/1974 | Steinmann | 318/483 X |
| 4,554,493 | 11/1985 | Armstrong | 318/483 X |
| 4,613,802 | 9/1986 | Kraus et al. | 318/483 |
| 4,703,237 | 10/1987 | Hochstein | 318/483 |
| 4,740,735 | 4/1988 | Hayashi | 318/483 |
| 4,748,390 | 5/1988 | Okushima et al. | 318/483 |
| 4,805,070 | 2/1989 | Koontz et al. | 361/286 |
| 4,827,198 | 5/1989 | Mueller et al. | 318/483 |
| 4,942,349 | 7/1990 | Millerd et al. | 318/483 |
| 4,983,896 | 1/1991 | Sugiyama et al. | 318/286 |

FOREIGN PATENT DOCUMENTS 60-104419 10/1985 Japan.
2189906 11/1987 United Kingdom.

Primary Examiner—Bentsu Ro
Attorney, Agent, or Firm—Anderson Kill Olick & Oshinsky

[57] ABSTRACT

A rain-actuated control for covering systems makes it possible to obtain a device capable of automatically closing open coverings in the event of rain. The device must be simple and easy to mount in existing installations. The rain-actuated control comprises a sensor consisting of two electrodes (1,15) with an intermediate layer of glass (13) and air (29) which functions as a capacitor. When rain is deposited (30) on the glass, the dielectric constant of the glass is changed, and signals are generated, which cause the control system to close the covering system. Automobile windows and automobile bodies can be used advantageously as elements of the capacitor.

7 Claims, 4 Drawing Sheets

RAIN-ACTUATED CONTROL FOR COVERING SYSTEMS

The invention relates to a rain-actuated control for covering systems, which can be used, for example, for sliding roofs and lifter roofs of sheds, arenas, automobiles and greenhouses, etc.

The invention starts out from a sensor element, which is or will be mounted at the site to be monitored and passes on signals over a control system to a suitable actuating system.

The closing of covering systems for sheds, arenas, greenhouses, convertibles and sliding-lifter roofs of motor vehicles must usually be carried out at the present time by manually activating a switch, closing the circuit of which starts the closing of the covering, even though sensors of different types are known, which make the automatic closing of the covering possible in the event of rain. However, the problem arises here that a retrofitted or serial installation of such sensors with an appropriate and adapted electronic circuit is associated with much effort and consequently with additional costs.

It is an object of the invention, starting out from the control, to close a covering in the open position automatically with simple means in the event of precipitation.

A capacitor is an arrangement of insulated electrodes. For all arrangements with the same geometric data and the same dielectric properties of the insulating medium between the electrodes, the ratio of charge to voltage, which is referred to as the capacitance of the capacitor, has the same value.

With such a control, covering systems, that is, roof and wall parts of sheds and arenas of any type, sliding and lifter roofs of automobiles, roofs of convertibles and roofs and wall parts of greenhouses of the horticulture trade, if in the open position, can be closed automatically.

Suitable for use as capacitor electrodes in automobiles are the sheet metal body and the heating wires of the electrical windshield heater, which, with the ignition switched off, are connected galvanically, for example, by relay contacts, separately from the regular supply connections and are connected instead with the electronics measuring the capacitance. This sensor accordingly is already integrated in almost any modern automobile.

Since the vehicle geometry remains unchanged, the capacitance between the sheet metal body and the heating wires of the windshield heater changes only if there is a change in the dielectric in the electrostatic field of the capacitor.

Brief changes in the dielectric due to the intrusion of persons or animals into the relevant electrostatic field can be compensated for by the microprocessor control, as can normal soiling or contamination, which takes place relatively slowly, as well as interfering influences of a nonrecurring nature, such as bird droppings or a wind-blown wet leaf within the electrostatic field. The effect of temperatures is of such insignificant importance, that it can also be compensated for without problems. Through manipulating the control, a new normal capacitance can be stored at any time.

A further advantage is the protection of the sensor against corrosive media, since this sensor is especially in the protected interior of the automobile or consists of the sheet metal of the vehicle.

In the case of convertibles, in which the possibly heated rear window is lowered during the precipitation-monitoring time and thus does not come into consideration as sensor, a substitute electrode can be installed with a minimum of effort. This substitute electrode consists of a conducting and pressure sensitive foil, which is affixed to the upper edge of the inside of the windshield without a galvanic connection to the sheet metal of the automobile. This conductive foil is permanently connected to the microprocessor circuit.

The capacitor principle can, however, be used not only with automobiles.

The construction of the capacitor is very simple. It consists merely of two electrodes, which are insulated from one another. The insulation is retained under all types of weathering influences. This capacitor can then be mounted at any suitable place on buildings and connected with the microprocessor control.

The microprocessor control is in a position not only to control the actuating system independently of the position of the covering, but also to fulfill the usual safety guarantees, which consist of stopping the actuating system promptly when there is jamming or catching.

Since the ability to control the installation depends on the sensitivity of the sensor, special importance is attached to the construction of the sensor, which runs out to as large as possible a two dimensional development of the electrodes. Due to a meandering arrangement of the electrodes, large electrode surfaces are obtained in the smallest space. These electrode surfaces are able to record the smallest changes in the dielectric. However, the meander-shaped electrode arrangement, which is combined into a compact structural unit, cannot be installed in all areas of use unobtrusively and without interfering with the total picture at the respective place of use. The sensor that is to be used in automobiles must therefore experience a special refinement. The control system for a use in automobiles should be well adaptable to the actualities there and—also as retrofitted equipment—should require only little expenditure.

The expression, the similarity of two-dimensionally constructed electrodes, is intended to mean sufficiently large metal surfaces, which, with an intervening space of glass and air, form a capacitor. Such metal surfaces can be put in position with little effort and unobtrusively, for example, as metal foil or as vapor-deposited metal strips on automobile windows. With the mounting of the oscillator in the immediate vicinity of an electrode, a sufficient sensitivity is achieved without having to increase the expenditure for control elements.

If an electrode is installed as a conductive strip between the wires of the rear window, the remaining parts of the vehicle, such as the body and the glass of the rear window, can be used as elements of a capacitor. By these means, the invention can be realized with little expenditure. As retrofitted equipment in automobiles, only an additional control unit is required aside from the conductive strip on the rear window with the oscillator.

A particular advantage is achieved if, when installing the rear window heating wires, an additional conductive strip is put in position and interconnected as a sensor electrode.

If there is no suitable rear window in the automobile, as, for example, in convertibles, the strip-shaped electrode can be mounted as a conductive foil or as a vapor-deposited metal strip. With this equipment, the open top of a convertible can be closed automatically when it starts to rain.

By constructing the control on the basis of a microprocessor and providing a control kit with few individual parts, relatively inexpensive equipment is achieved for retrofitting purposes as well as for serial installation.

The invention is explained in the following on examples of the operation by means of some Figures.

Figure 1:
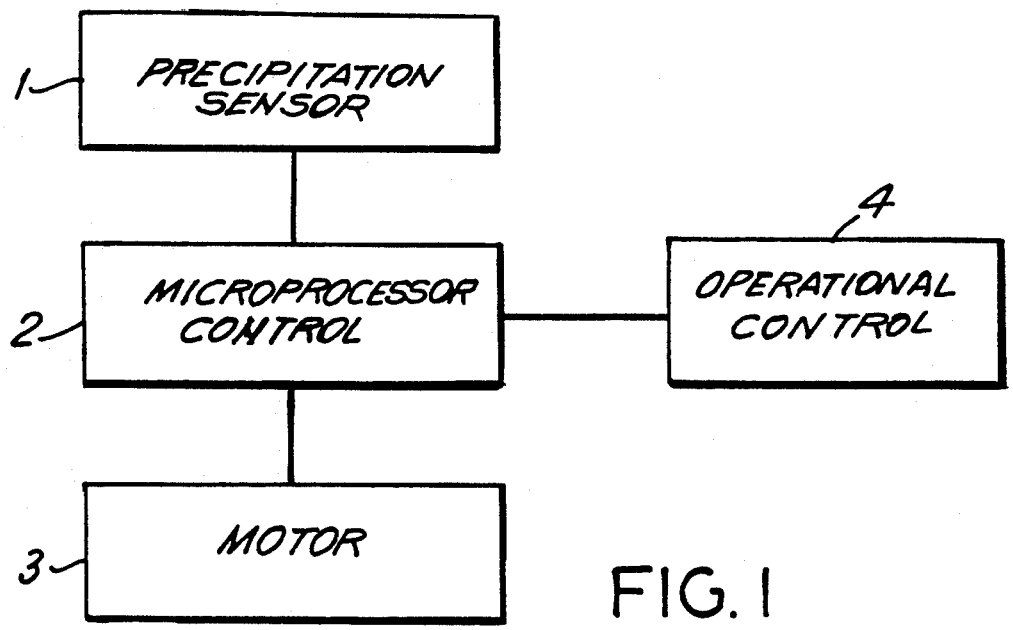
FIG. 1 shows a block circuit diagram.

By means of a block circuit diagram, it is shown in FIG. 1 that the sensor 1 is in direct contact with the microprocessor control 2. The driving motor 3 and the operating element 4, for example, an on-button and an off-button, are standard equipment in automobiles with an electric sliding roof; likewise, almost all modern automobiles are equipped with rear window heating.

Figure 2:
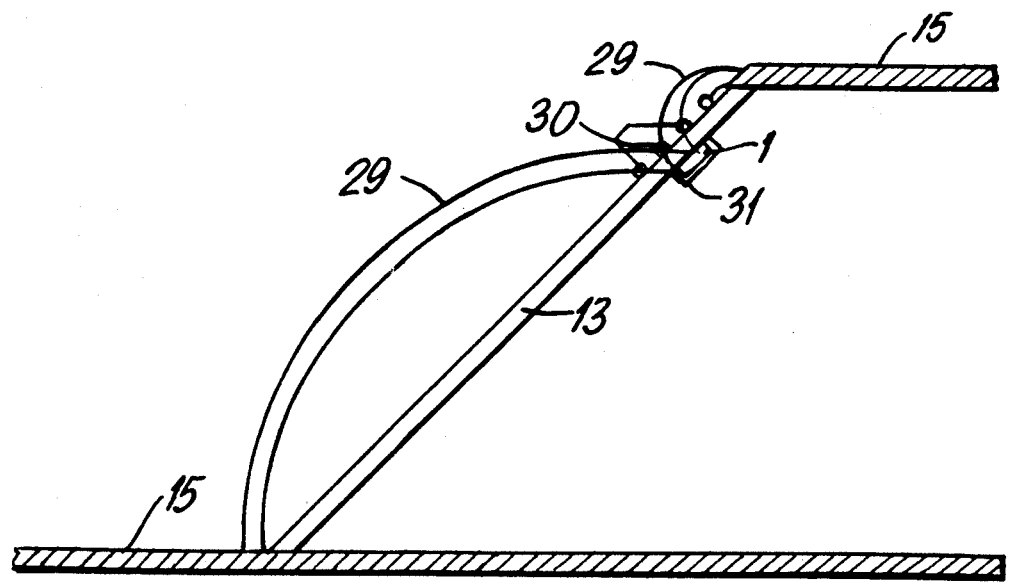
FIG. 2 shows a sensor.

FIG. 2 shows in the cross section of an automobile rear sensor, which consists of a strip-shaped electrode 1, an insulation 31, the car body 15 and the rear window 13. By applying a direct-current voltage of 5 V to the electrode 1, an electrical field 29 is developed between the strip shaped electrode and the car body 15. If the electrical field constant, which has arisen through this arrangement, is multiplied by the dielectric number of glass and air, the dielectric constant $\epsilon$ of the dielectric is obtained. When precipitation starts, such as rain 30 on the rear window 13, the factor of the dielectric number of water $\epsilon_r$, depending on the amount of precipitation, is multiplied by the factor of the electric field constant $\epsilon_o$. An increase in the capacitance is thus achieved due to the charge on the two carrier electrodes 1 and 15, which is influenced additionally by the stray field.

Figure 3:
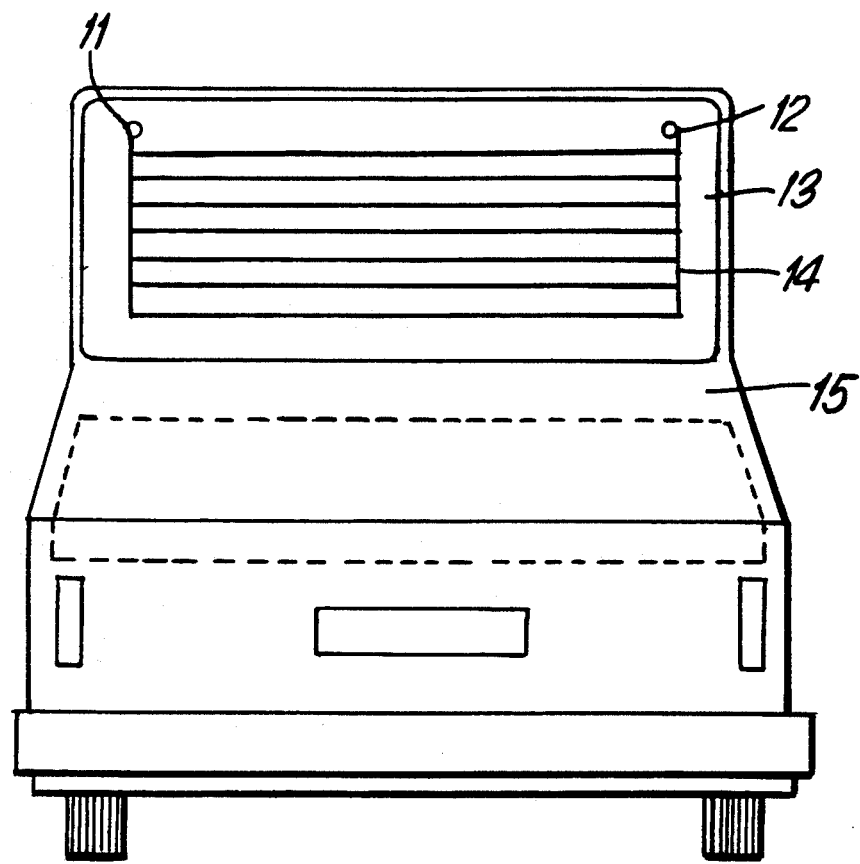
FIG. 3 shows an automobile rear.

FIG. 3 shows the sensor and an automobile rear with a rear window heater 14 on a glass rear window 13, which acts as insulation between the two capacitor electrodes, namely the rear window heater 14 and the sheet metal 15 of the automobile. When used as electrode, the connections 11 and 12 are severed from the heater supply and connected instead to the microprocessor control.

Figure 4:
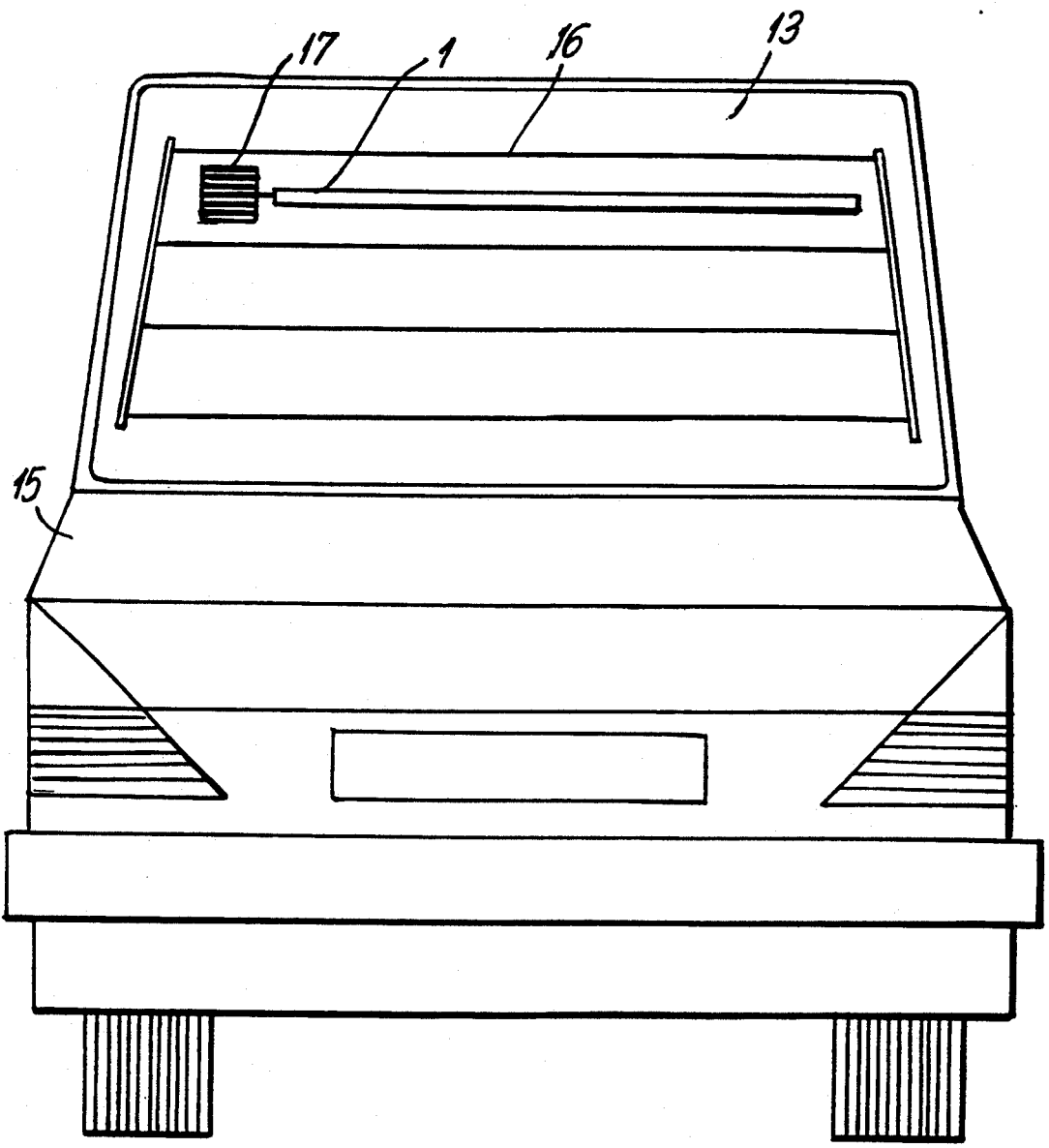
FIG. 4 shows a sensor mounted with a rear window heater at the rear window of an automobile.

The sensor, which is shown in FIG. 4, consists of a strip-shaped conductor 1, which is mounted between the heating wires 16 of a rear window heater on a rear window 13, the glass of the rear window 13 and air acting as dielectric and the metal surface 15 of the automobile body acting as second electrode, in order to produce the capacitor effect in this manner. If now the rear window 13 is affected by precipitation, such as rain or snow, the dielectric changes, as a result of which the oscillator 17 changes its frequency and passes this on to the microprocessor 18. As a function of the frequency change, the microprocessor 18 passes on control signals to the actuating system of the cover.

Figure 5:
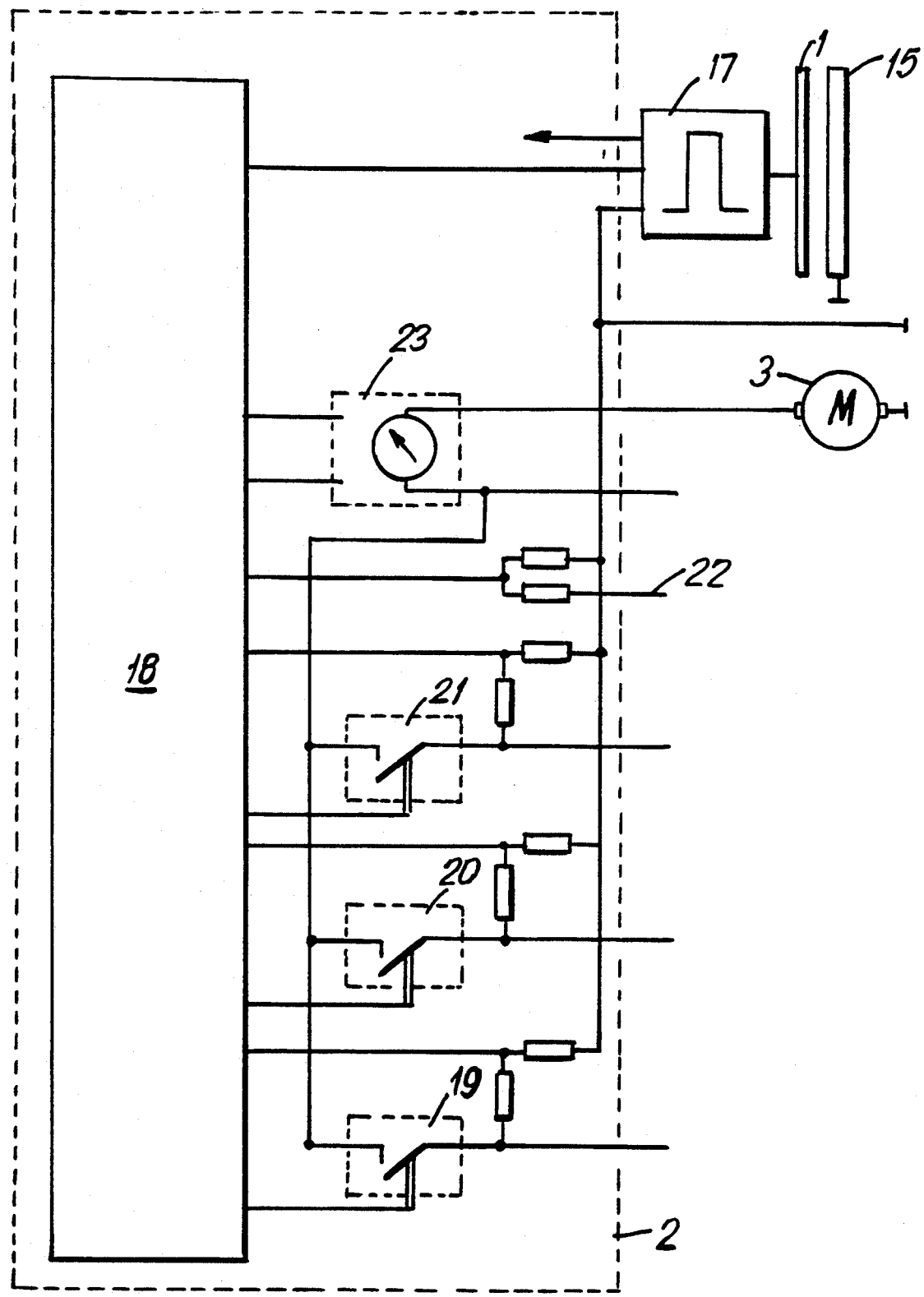
FIG. 5 shows a block circuit diagram of a microprocessor control.

The block circuit diagram of the whole control system is shown in FIG. 5. It can be seen that this control system consists of a microprocessor control 2. The use of a microprocessor 18 has the advantage that increases in precipitation as well as drying processes and conditions of constant dielectric are determined and flow into the command execution. Electronic switches, with which the closing and opening processes of the sliding and lifter roof can be selected, are labeled 19 to 21. The connecting lead 22 to the ignition lock is labeled 22. This connecting lead 22 makes the automatic system inoperative when the ignition is switched on. When the ignition is switched off, the frequency of the oscillator 17 is stored as the basic frequency, which corresponds to the respective state of the dielectric on the rear window (dirt, wetness, snow coverage). This process is repeated for each position of the covering system, which is achieved by manual switch operation and for drying processes of the glass, on which the sensor is mounted. As already mentioned in the explanation for FIG. 4, the oscillator is labelled 17, the strip-shaped conductor 1 and the metal surface of the automobile body 15.

For safety reasons, the microprocessor control 2 has a current monitor 23. If a resistance is encountered during the closing process of the covering system—due to any part that has jammed—the driving current increases. This is a signal for countermanding the closing process. After that, the closing process is initiated again several times, until it is finally switched off. The automatic closing process can be interrupted at any time by switching on the ignition or by manually operating the switches of the sliding/lifter roof operational controls.

Figure 6:
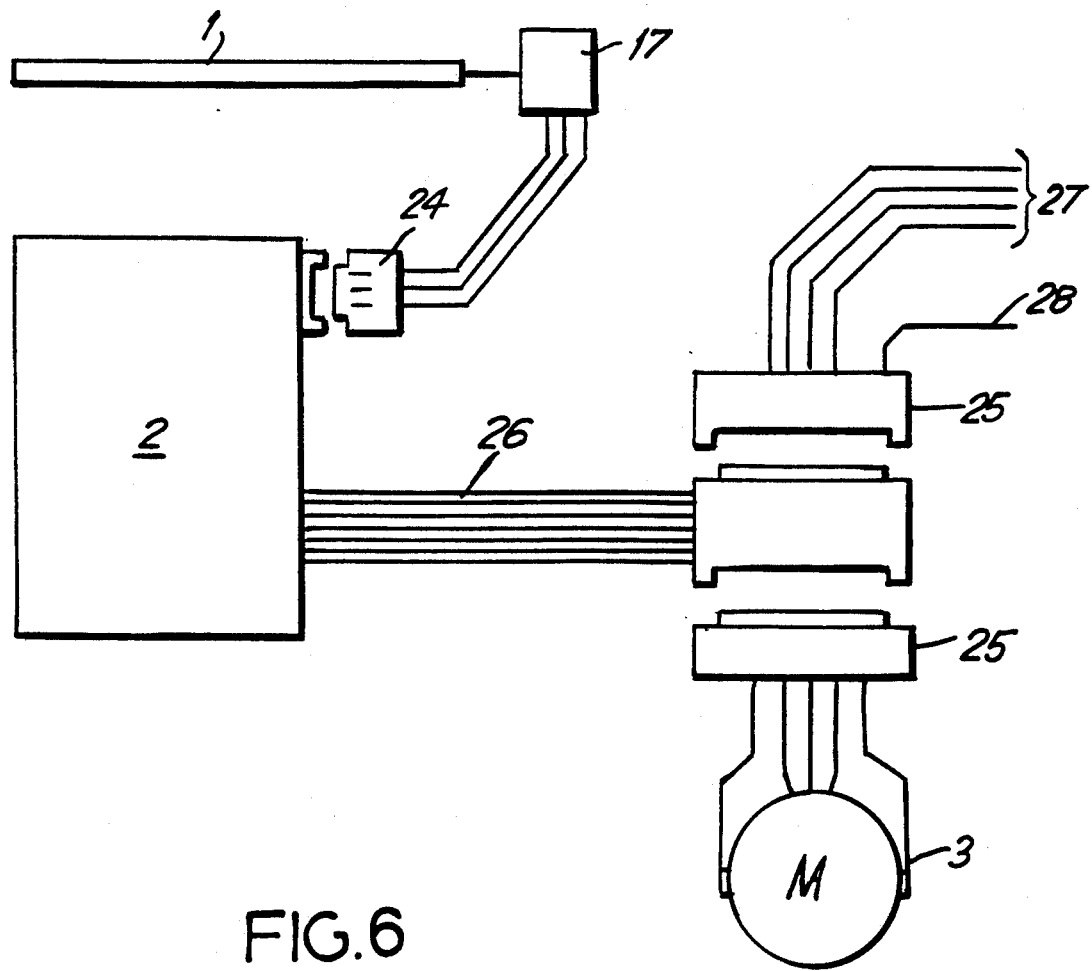
FIG. 6 shows an embodiment of a kit of a rain-actuated control for a covering system.

A kit for retrofitting purposes or for serial installation is shown in FIG. 6. According to this, the oscillator 17 is connected over a connector 24 with the microprocessor control 2, which is accomodated at a suitable site in the interior of the automobile. For the additional installation (subsequently of serially), the sensor control is connected by means of a cable 26 from the microprocessor control 2 to the junction 25 of the drive cable 27 with the 12 volt continuous supply 28 and the connection point of the drive motor 3.

I claim:

1. A rain-actuated control for a vehicle covering system having a driving motor (3) for controlling a vehicle covering, comprising:
   a sensor (1) responsive to the presence of precipitation,
   a microprocessor control for setting in motion the driving motor (3) in response to a signal from the sensor,
   said sensor comprising:
   (i) a capacitor having electrodes and a dielectric material exposed to the precipitation, said capacitor changes its capacity as a function of the dielectric material which is in the electrostatic field of the capacitor electrodes in response to the presence of precipitation,
   (ii) said capacitor comprising, as the electrodes, a window heater (14) and the sheet metal (15) of the vehicle body, with the glass (13) on which the heater is mounted serving as an insulating layer between the electrodes.

2. The rain-actuated control of claim 1, wherein the insulating layer between the capacitor electrodes has the properties that it is stable at high and low temperatures, resistant to the effects of acid and retains its insulating properties when exposed to UV radiation and does not change its dielectric properties or changes them only very slowly when subjected to such exposure.

3. The rain-actuated control of claim 1, wherein the sensor (1) is formed from two two-dimensional and similarly configured, mutually insulated and spaced-apart electrodes, the gap between the electrodes consisting of glass and air as dielectric, and an oscillator (17) connected in the immediate vicinity to one of the two electrodes and which passes a signal to the microprocessor control, the capacitance of the sensor determining the oscillator frequency.

4. The rain-actuated control of claim 3, wherein the one electrode is an electrically conductive strip, which is installed between the heating wires (16) of the rear window (13) of an automobile at a distance from and insulated from the heating wires, while the other electrode is the electrically conducting vehicle mass, and the dielectric is the rear window glass and air.

5. The rain-actuated control of claim 1, further comprising:
an oscillator circuit, said capacitor being connected as a frequency-determining component of the oscillator circuit,
said microprocessor control including means for detecting a frequency change of the oscillator circuit.

6. The rain-actuated control of claim 5, wherein the precipitation serves as dielectric and, with that, brings about a measurable change in the capacitance of the capacitor.

7. A rain-actuated control for a covering system having a driving motor (3) for controlling a covering, comprising:
a sensor (1) responsive to the presence of precipitation,
a microprocessor control for setting in motion the driving motor (3) in response to a signal from the sensor,
said sensor comprising:
(i) a capacitor having electrodes and a dielectric material exposed to the precipitation, said capacitor changes its capacity as a function of the dielectric material which is in the electrostatic field of the capacitor electrodes in response to the presence of precipitation, one of the electrodes being a vapor-deposited metal strip or a metal foil on the windshield and another of the electrodes being the electrically conducting vehicle mass,
an oscillator circuit, said capacitor being connected as a frequency-determining component of the oscillator circuit,
said microprocessor control being connected for detecting a frequency change of the oscillator circuit.

* * * * *